United States Patent [19]

Leichnitz et al.

[11] Patent Number: 4,769,218
[45] Date of Patent: Sep. 6, 1988

[54] TEST TUBE WITH FLAME ARRESTER FOR COMBUSTIBLE GASES

[75] Inventors: Kurt Leichnitz, Gross Gröaun; Hans Matthiessen, Gross Parin, both of Fed. Rep. of Germany

[73] Assignee: Drägerwerk Aktiengesellschaft, Fed. Rep. of Germany

[21] Appl. No.: 62,772

[22] Filed: Jun. 15, 1987

[30] Foreign Application Priority Data

Jun. 24, 1986 [DE] Fed. Rep. of Germany ....... 3621075

[51] Int. Cl.⁴ .......................... G01J 1/48; G05B 9/06
[52] U.S. Cl. ..................................... 422/86; 422/117
[58] Field of Search ........................... 422/86, 117, 78

[56] References Cited

U.S. PATENT DOCUMENTS

| | | | |
|---|---|---|---|
| 4,046,014 | 9/1977 | Boehringer et al. | 73/863.12 |
| 4,077,776 | 3/1978 | Möller et al. | 422/83 |
| 4,159,304 | 6/1979 | Shono | 422/59 |
| 4,389,372 | 6/1983 | Lalin | 422/86 |

FOREIGN PATENT DOCUMENTS 1974909 12/1967 Fed. Rep. of Germany .
0276497 7/1978 U.S.S.R. ................. 422/98

Primary Examiner—Benoit Castel
Assistant Examiner—Lyle Alfandary-Alexander
Attorney, Agent, or Firm—McGlew and Tuttle

[57] ABSTRACT

A test tube for combustible gases is intended to be provided with protective devices, so that, in proving the presence of combustible gases, it cannot become an ignition source. To that end, a flame arrester is arranged in front of and/or behind the test material.

6 Claims, 1 Drawing Sheet

TEST TUBE WITH FLAME ARRESTER FOR COMBUSTIBLE GASES

FIELD AND BACKGROUND OF THE INVENTION

This invention relates in general to devices for testing for presence of various gases and in particular to a new and useful test tube having a flame arrester for ensuring that the gases do not ignite.

A test tube of this nature is known from DE-GM 19 74 909.

For detecting various combustible gases with test tubes, cayalysts are introduced into the test tube to obtain reaction products, the presence of which can be demonstrated. These catalysts convert the gas to be detected, giving off considerable heat (for example, hydrogen with air oxygen in the presence of palladium or hopcalite). Other gases, as for instance, carbon bisulphide and hydrogen sulphide, indicate exothermic reactions with the test material in the indicator. In all these cases, high reaction temperatures can occur with high concentrations in the test tube. On exceeding a given concentration limit (lower explosion limit), the gas mixture becomes explosive so that there is the danger that the test tube with its high reaction temperatures becomes the ignition source.

From U.S. Pat. No. 4,159,304 a housing permitting through-flow for receiving a test tube is known. The known housing serves to protect the test tube from mechanical damage while being taken along by its carrier during working periods under difficult conditions, as they, for example, exist in factory installations. The known housing has connections for taking in a gas sample over a feed pump, so that the gas sample can stream through the test tube contained in the housing when the ends of the test tube are open. To detect the presence of any possible harmful substances in the gas sample, the housing can be screwed apart and the test tube taken out. Propagation into the environment of an ignition possibly caused by the test tube is not prevented by this measure.

SUMMARY OF THE INVENTION

The invention provides a test tube with protective devices such that in detecting the presence of combustible gases it cannot become a source for an ignition.

The solution of the task is accomplished by arranging in front of and/or behind the test substance a flame arrester.

The advantage achieved through the invention lies mainly in the fact that the heated gas mixture obtained with high test material concentrations in the test tube do not spread and lead to ignition of an explosive gas mixture in the environment of the apparatus carrier.

The flame arresters are expediently set into the tips of the customarily used glass tubes. The glass insulates the occurring reaction temperature to such an extent that the surface temperature of the glass does not reach ignition temperatures. The test tubes can still be set into the known housings as is customarily the case.

To increase operating safety, the test tube can be contained in a protective housing, which also contains the flame arresters. The flame arresters can be designed larger and with lower stream resistance and can be used repeatedly with different test tubes. In this case, it is not necessary that the test tubes themselves are provided with flame arresters.

The flame arresters are advantageously arranged in an intake and an outlet nozzle of the housing. Both nozzles can be connected screwably with the housing so that exchanging the flame arresters and the test tube is readily possible.

Accordingly it is an object of the invention to provide a test tube for combustible gases which has a hollow interior which defines a gas test flow passage through with a reacting material in the passage and having at least one openable end for the flow of gases there through and at least one flame arrester adjacent the openable end.

A further object of the invention is to provide a gas testing device which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENTS

Figures 1, 2:
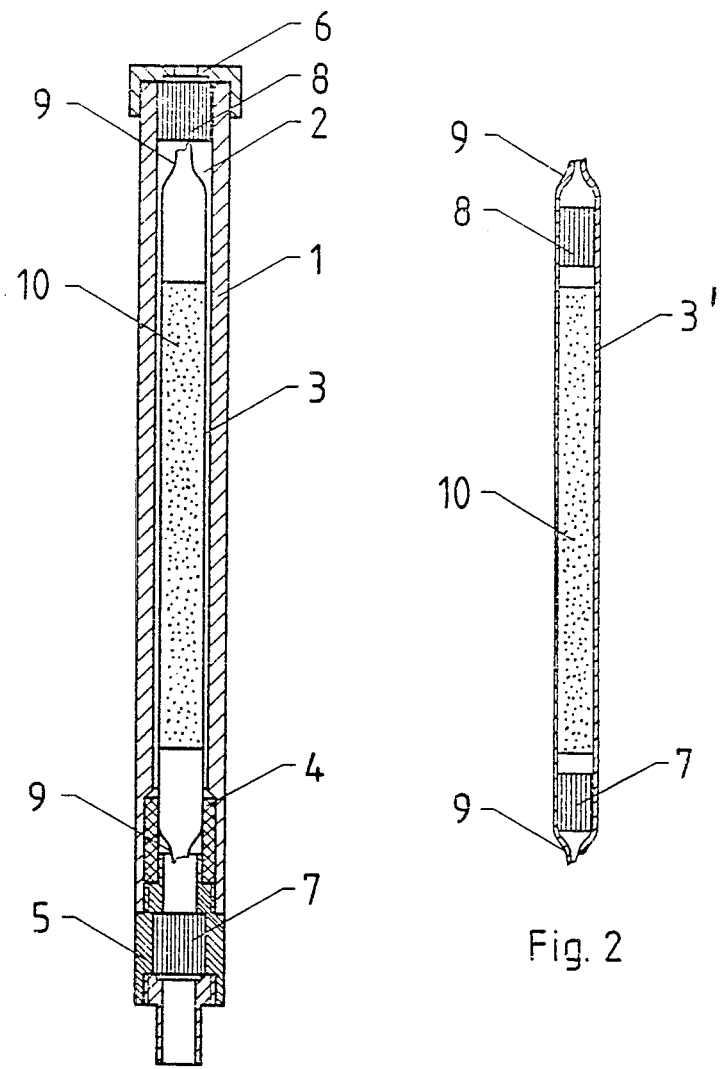
FIG. 1 is a cross section through the housing with an inset test tube, constructed in accordance with the invention.
FIG. 2 is a cross section through a test tube with flame arresters of another embodiment of the invention.

Referring to the drawings in particular the invention embodied therein in FIGS. 1 and 2 comprises a transparent test tube designated 3 in FIGS. 1 and 3' in FIG. 2 which has a hollow interior which defines a gas test flow passage having a reactant material such as a color indicator 10 therein. Each tube 3 and 3' includes an openable end having a frangible tip 9 which is open at each end to permit the flow of gases through the tube. In accordance with the invention at least one flame arrester 8 is located in the vicinity of at least one of the ends and as indicated in the drawings may be in the path of flow at each end of the test tubes 3 and 3'.

In FIG. 1 a transparent housing 1 is shown in cross section, which contains in its oblong tubular hollow space 2 a test tube 3, which is held in a holder 4. Both ends of the housing 1 are provided with an intake nozzle 5 for connecting a feed pump (not shown) and with an inlet nozzle 6 for letting in the gas mixture to be tested. The intake nozzle 5 can be screwed into the housing 1 with corresponding threads and is provided with a lip. The inlet nozzle 6 is formed as a cap which can be set on the end of the housing 1. In the intake nozzle 5 as well as in the inlet nozzle 6 flame arresters 7 and 8 are installed. These flame arresters can be known sintered metal discs or they can comprise of a bundle of suitable capillary tubes.

The gas taken in through the inlet nozzle 6 enters through the flame arrester 8 into the hollow space 2 and from there passes through the opened tips 9 of the test tube 3 through the flame arrester 7 of the intake nozzle 5. During the passage of the gas sample through the test tube 3 the harmful substance is converted in the color indicator 10. The gas heated in the exothermic reaction cannot become an ignition source for the gas mixture existing in the environment because of the two flame arresters 7 and 8.

The test tube 3' shown in cross section in FIG. 2 which includes the color indicator 10 contains in both of its tips 9 the flame arresters.

What is claimed is:

1. A test tube for combustible gases to be detected comprising a glass tube having breakable tips at each end which, when broken, define openings at each end of said glass tube, a material in said tube which is reactable with a gas to be detected and providing an increased temperature of the gas upon reaction, and a flame arrester in said glass tube adjacent at least one of said breakable tips and being in the form of a bundle of capillary tubes defining said small-sized flow openings therethrough, said test tube defining a gas flow passage for a combustible gas to be detected into one end of said glass tube and through said flame arrester out through the opposite end of said tube.

2. A test tube according to claim 1 wherein there is a flame arrester adjacent to each end.

3. A test tube according to claim 1 including an exterior housing in which said test tube is positioned having an opening at each end of said housing for the flow of gases through the housing and through said tube and wherein said flame arrester is located in said housing adjacent said openable end.

4. A test tube according to claim 3 including a flame arrester contained in said housing adjacent each end and each of said test tubes being openable at each end.

5. A test tube according to claim 1 including an outer transparent housing having an opening at each end alignable with an openable end of each end of said test tube, each end of said test tube being open and said housing having a nozzle adjacent each end with a flame arrester in each said nozzle.

6. A testing device for detecting combustible gases, comprising an outer glass tube having one end with an inlet end, said outer glass tube having an inlet nozzle adjacent to said inlet end, a flame arrester in said inlet nozzle of a material defining small passage for the flow of gas therethrough and inhibiting flame propagation, said flame arrester being in the form of a bundle of capillary tubes, said nozzle having a tubular portion extending into said outer glass tube and providing a connection passage, a glass indicator tube arranged inside said outer glass tube and having a frangible tip which is breakable and arranged in said connection passage and having an opposite end with a frangible tip, a second flame arrester arranged exteriorly of said frangible tip in said outer glass tube and a cover over said outer glass tube having a flow opening therethrough for the gas to be detected.

* * * * *